United States Patent
Stahl et al.

(10) Patent No.: US 11,458,334 B2
(45) Date of Patent: Oct. 4, 2022

(54) SYSTEM AND METHOD FOR DIAGNOSIS AND TREATMENT

(71) Applicant: SHANGHAI UNITED IMAGING HEALTHCARE CO., LTD., Shanghai (CN)

(72) Inventors: Johannes Stahl, Houston, TX (US); Supratik Bose, Houston, TX (US); Li Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/114,431

(22) Filed: Dec. 7, 2020

(65) Prior Publication Data
US 2021/0090291 A1     Mar. 25, 2021

Related U.S. Application Data

(63) Continuation-in-part of application No. 16/217,258, filed on Dec. 12, 2018, now Pat. No. 10,857,391, (Continued)

(51) Int. Cl.
*A61N 5/10*     (2006.01)
*A61B 6/04*     (2006.01)

(52) U.S. Cl.
CPC .......... *A61N 5/1049* (2013.01); *A61B 6/0407* (2013.01); *A61B 6/0492* (2013.01); *A61N 5/1069* (2013.01); *G06T 2207/30204* (2013.01)

(58) Field of Classification Search
CPC ..... A61B 6/0407; A61B 6/032; A61B 6/0457; A61B 6/0492; A61N 2005/1052; (Continued)

(56) References Cited

U.S. PATENT DOCUMENTS 5,386,446 A    1/1995    Fujimoto et al.
7,221,733 B1    5/2007    Takai et al.
(Continued)

FOREIGN PATENT DOCUMENTS

CN    102049106 A    5/2011
CN    104161533 A    11/2014
(Continued)

OTHER PUBLICATIONS

International Search Report in PCT/CN2017/115946 dated Aug. 29, 2018, 4 pages.
(Continued)

*Primary Examiner* — Chih-Cheng Kao
(74) *Attorney, Agent, or Firm* — Metis IP LLC

(57) ABSTRACT

A method may include acquiring a first image including a target point and a first reference point, the target point corresponding to at least one part of a subject, the first reference point corresponding to a first marker disposed on the couch of the medical device; determining a first spatial position of the first marker, the first spatial position corresponding to a first working position of the couch; determining a first spatial position of the at least one part of the subject based on the first image and the first spatial position of the first marker; determining a second spatial position of the first marker, the second spatial position corresponding to a second working position of the couch; determining a second spatial position of the at least one part of the subject based on the second spatial position of the first marker and the first spatial position of the at least one part of the subject. In some embodiments, the method may further include adjusting the second working position of the couch based on the second spatial position of the at least one part of the subject.

20 Claims, 8 Drawing Sheets

Related U.S. Application Data which is a continuation of application No. PCT/CN2017/115946, filed on Dec. 13, 2017.

(58) Field of Classification Search
CPC .... A61N 2005/1055; A61N 2005/1058; A61N 2005/1059; A61N 2005/1061; A61N 2005/1063; A61N 5/1039; A61N 5/1042; A61N 5/1049; A61N 5/1069; A61N 2005/105

See application file for complete search history.

(56) References Cited

U.S. PATENT DOCUMENTS

| | | |
|---|---|---|
| 2004/0082852 A1 | 4/2004 | Cherek et al. |
| 2007/0016001 A1 | 1/2007 | Graf |
| 2007/0238950 A1 | 10/2007 | Vija et al. |
| 2008/0031414 A1 | 2/2008 | Coppens |
| 2008/0123924 A1 | 5/2008 | Nabatame et al. |
| 2011/0196223 A1 | 8/2011 | Balakin |
| 2013/0114871 A1 | 5/2013 | Berkus et al. |
| 2014/0275698 A1 | 9/2014 | Lidström et al. |
| 2016/0067525 A1 | 3/2016 | Bouchet et al. |
| 2017/0189719 A1 | 7/2017 | Liu et al. |
| 2017/0189720 A1 | 7/2017 | Liu et al. |
| 2017/0189724 A1 | 7/2017 | Liu et al. |
| 2017/0340902 A1 | 11/2017 | Vilsmeier et al. |

FOREIGN PATENT DOCUMENTS

| | | |
|---|---|---|
| CN | 106175810 A | 12/2016 |
| CN | 107096135 A | 8/2017 |
| WO | 2016206743 A1 | 12/2016 |

OTHER PUBLICATIONS

Written Opinion in PCT/CN2017/115946 dated Aug. 29, 2018, 4 pages.

SYSTEM AND METHOD FOR DIAGNOSIS AND TREATMENT

CROSS-REFERENCE TO RELATED APPLICATIONS

This application is a continuation-in-part of U.S. application Ser. No. 16/217,258, filed on Dec. 12, 2018, which is a continuation of International Application No. PCT/CN2017/115946, filed on Dec. 13, 2017, the entire contents of which are hereby incorporated by reference.

TECHNICAL FIELD

The present disclosure generally relates to medical diagnosis and treatment system, and more specifically relates to methods and systems for positioning at least one part of a subject in a medical procedure.

BACKGROUND

Various imaging techniques have been widely used in medical diagnosis, radiation therapy planning, surgery planning and other medical procedures, such as an X-ray photography, a magnetic resonance imaging (MRI), a computed tomography (CT), a positron emission tomography (PET), etc. Generally, a couch may be used to support and/or transfer a subject to be examined to a scanning region of an imaging device and/or a treatment device. In some embodiments, a couch loaded with the subject (e.g., a patient) may sag or deflect in a medical procedure. For example, in a multi-modality imaging, the couch may sag when the couch is extended along the longitudinal direction of the couch to scanning regions of the multi-modality imaging devices, causing poor image qualities and imprecise fused images. As another example, in a diagnosis and treatment procedure, the couch may sag when the couch is moved from an imaging device to a treatment device, causing inaccurate positioning of a target point (e.g., an anatomical point). Further, when using a conventional Fan-Beam CT for IGRT, the couch has to be moved between a treatment position and a CT imaging position. This is an inherent drawback compared to in-situ CBCT where the image is taken in the treatment position. Because of this, any error in the movement of the couch from one position to the other and vice versa, will be an additional error on top of all other imaging errors. Thus, it is desirable to provide systems which allow a mapping from the image coordinate system to the treatment coordinate system such that a spatial position of at least one part of a subject in a medical procedure can be accurately determined.

SUMMARY

According to an aspect of the present disclosure, a method for determining a spatial position of at least one part of a subject in a medical procedure is provided. The method may be implemented on at least one machine each of which has at least one processor and storage. The method may include acquiring a first image including a target point and a first reference point, the target point corresponding to at least one part of a subject, the first reference point corresponding to a first marker disposed on the couch of the medical device; determining a first spatial position of the first marker, the first spatial position corresponding to a first working position of the couch; determining a first spatial position of the at least one part of the subject based on the first image and the first spatial position of the first marker; determining a second spatial position of the first marker, the second spatial position corresponding to a second working position of the couch; determining a second spatial position of the at least one part of the subject based on the second spatial position of the first marker and the first spatial position of the at least one part of the subject; and causing an adjustment of the second working position of the couch based on the second spatial position of the at least one part of the subject.

In some embodiments, the first marker may include at least one of a radiologically detectable marker or a radiologically and optically detectable marker.

In some embodiments, the first marker may be detected by at least one of a photoelectric sensor, a laser interferometer, or a camera.

In some embodiments, the first marker may be disposed inside the couch.

In some embodiments, the determining a first spatial position of the at least one part of the subject based on the first image may further include: determining first transformation data relating to a first coordinate system applied to the first image and a second coordinate system applied to the medical device; and determining the first spatial position of the at least one part of the subject based on the first spatial position of the first marker and the first transformation data.

In some embodiments, the determining a second spatial position of the first marker may further include: determining a first displacement of the first marker when the couch of the medical device moves from the first working position to the second working position based on a laser triangulation algorithm; and determining the second spatial position of the first marker based on the first displacement of the first marker.

In some embodiments, the determining a second spatial position of the first marker may further include determining a first spatial position of a second marker, the second marker being disposed on the couch of the medical device relative to the first marker; determining a second spatial position of the second marker; and determining the second spatial position of the first marker based on the first spatial position of the first marker, the first spatial position of the second marker, and the second spatial position of the second marker.

In some embodiments, the determining a second spatial position of the second marker may further include acquiring a second image including a second reference point, the second reference point corresponding to the second marker; and determining the second spatial position of the second marker based on the second image.

In some embodiments, the determining the second spatial position of the second marker based on the second image may further include determining second transformation data relating to a third coordinate system applied to the second image and the second coordinate system applied to the medical device; and determining the second spatial position of the second marker based on the second transformation data.

In some embodiments, the determining a second spatial position of the second marker may further include determining a second displacement of the second marker when the couch of the medical device moves from the first working position to the second working position based on a laser triangulation algorithm; and determining the second spatial position of the second marker based on the second displacement of the second marker and the first spatial position of the second marker.

In some embodiments, the second marker may include at least one portion of the couch.

In some embodiments, the second marker may be detected by at least one of a photoelectric sensor, a laser interferometer, or a camera.

In some embodiments, the second marker may include an optically detectable marker.

In some embodiments, the second marker may be disposed on a bottom of the couch.

According to an aspect of the present disclosure, a system for determining a spatial position of at least one part of a subject in a medical procedure is provided. The system may include a computer-readable storage medium storing executable instructions and at least one processor in communication with the computer-readable storage medium. When the executable instructions are executed, the executable instructions may cause the system to implement a method. The method may include may include acquiring a first image including a target point and a first reference point, the target point corresponding to at least one part of a subject, the first reference point corresponding to a first marker disposed on the couch of the medical device; determining a first spatial position of the first marker, the first spatial position corresponding to a first working position of the couch; determining a first spatial position of the at least one part of the subject based on the first image and the first spatial position of the first marker; determining a second spatial position of the first marker, the second spatial position corresponding to a second working position of the couch; determining a second spatial position of the at least one part of the subject based on the second spatial position of the first marker and the first spatial position of the at least one part of the subject; and causing an adjustment of the second working position of the couch based on the second spatial position of the at least one part of the subject.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include may include acquiring a first image including a target point and a first reference point, the target point corresponding to at least one part of a subject, the first reference point corresponding to a first marker disposed on the couch of the medical device; determining a first spatial position of the first marker, the first spatial position corresponding to a first working position of the couch; determining a first spatial position of the at least one part of the subject based on the first image and the first spatial position of the first marker; determining a second spatial position of the first marker, the second spatial position corresponding to a second working position of the couch; determining a second spatial position of the at least one part of the subject based on the second spatial position of the first marker and the first spatial position of the at least one part of the subject; and causing an adjustment of the second working position of the couch based on the second spatial position of the at least one part of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 3:
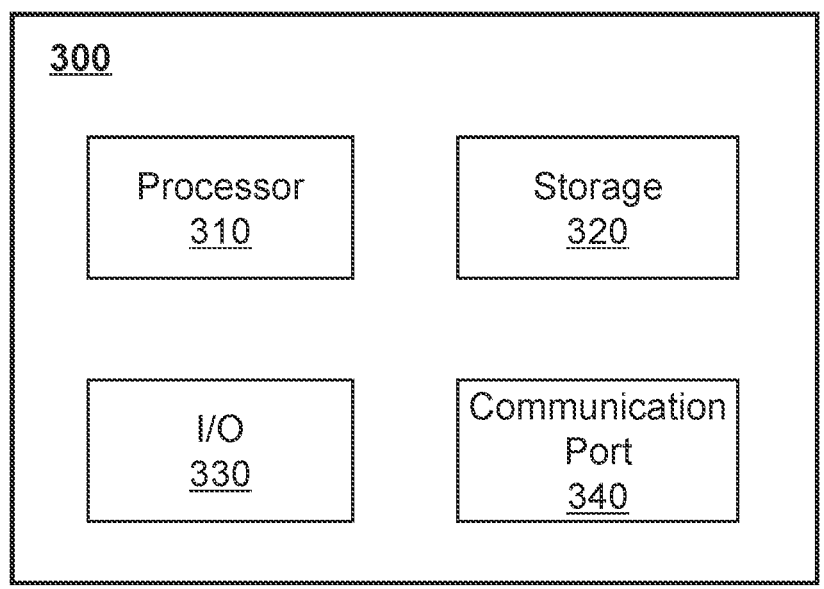
FIG. 3 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical diagnosis and/or treatment. In some embodiments, the medical system may include an diagnosis system. The diagnosis system may include a multi-modality imaging system. The multi-modality imaging system may include, for example, a computed tomography-positron emission tomography (CT-PET) system, a computed tomography-positron emission tomography-magnetic resonance imaging (CT-MRI) system, a X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a digital subtraction angiography-magnetic resonance imaging (DSA-MRI) system, or the like, or a combination thereof. In some embodiments, the medical system may include a diagnosis and treatment system. The diagnosis and treatment system may include a treatment plan system (TPS), an image-guide radio therapy (IGRT) system, etc. Merely by way of example, the image guided radio therapy (IGRT) system may include, for example, an CT guided radiotherapy system, an MRI guided radiotherapy system, etc.

The present disclosure relates to a system and method for determining a spatial position of at least one part of a subject to be treated in a radiotherapy procedure. The spatial position of the at least one part of the subject to be treated may be determined based on a spatial position of a marker disposed on a couch supporting the subject to be treated. According to the present disclosure, a mapping from the image coordinate system to the treatment coordinate system may be obtained by using one or more markers. The one or more markers may be disposed on the couch and/or on the subject to be treated. For example, a first spatial position of the marker may be determined when the couch is at an imaging device position. A first spatial position of the at least one part of the subject to be treated may be determined based on a radiological image acquired by the imaging device. A second spatial position of the marker may be determined when the couch moves from the imaging device position to a treatment device position. Then, a second spatial position of the at least one part of the subject to be treated may be determined based on the second spatial position of the first marker, the first spatial position of the first marker, and the first spatial position of the at least one part of the subject to be treated.

It should be noted that the diagnosis and treatment system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
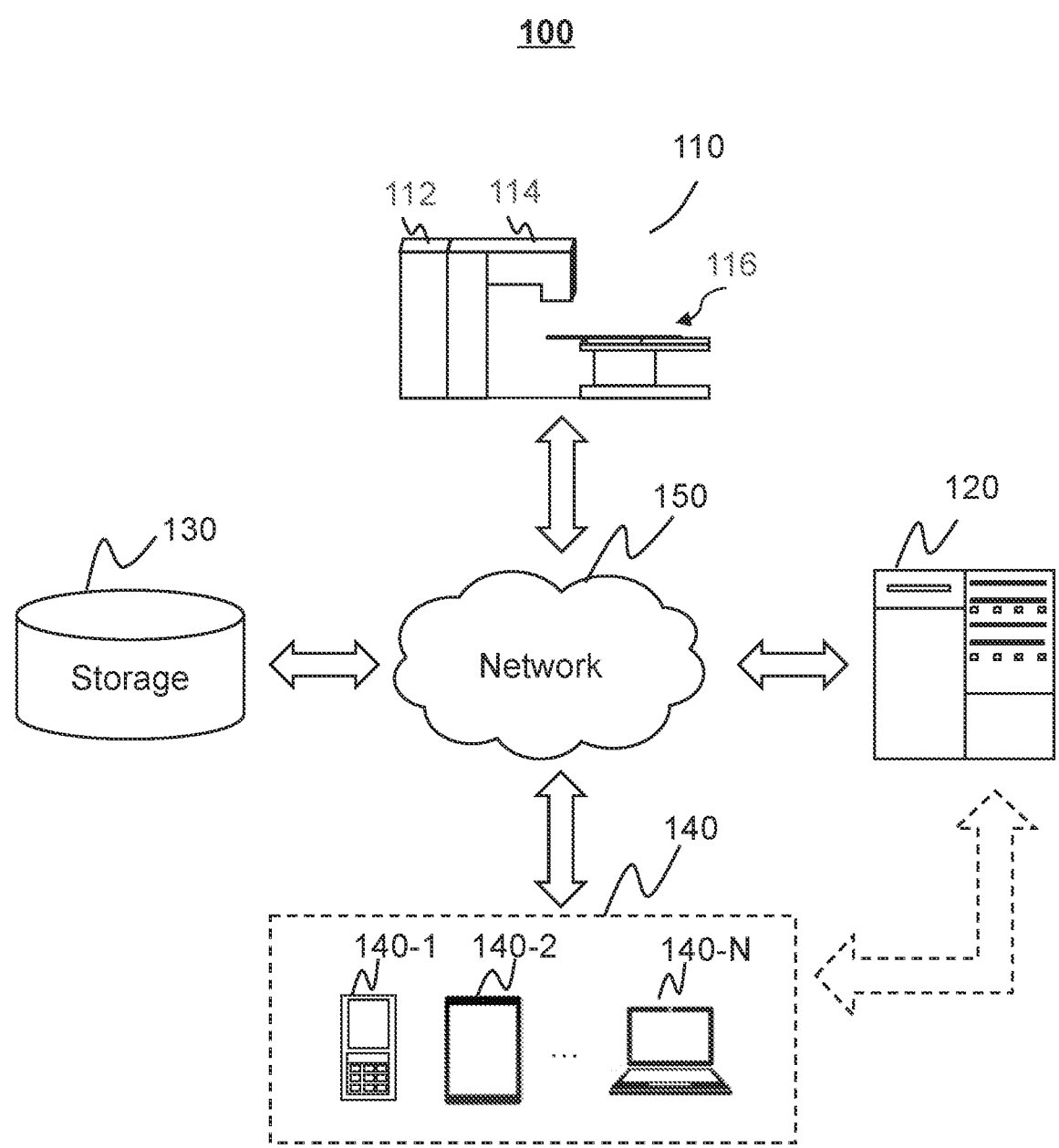
FIG. 1 is a schematic diagram illustrating an exemplary diagnosis and treatment system according to some embodiments of the present disclosure.

FIG. 1 is a schematic diagram illustrating an exemplary diagnosis and treatment system 100 according to some embodiments of the present disclosure. As shown, the diagnosis and treatment system 100 may include an image guided radio therapy (IGRT) apparatus 110, a processing device 120, a storage 130, one or more terminal(s) 140, and a network 150. In some embodiments, the IGRT apparatus 110, the processing device 120, the storage 130, and/or the terminal(s) 140 may be connected to and/or communicate with each other via a wireless connection (e.g., the network 150), a wired connection, or a combination thereof. The connections between the components in the diagnosis and treatment system 100 may vary. Merely by way of example, the IGRT apparatus 110 may be connected to the processing device 120 through the network 150, as illustrated in FIG. 1. As another example, the IGRT apparatus 110 may be connected to the processing device 120 directly. As a further example, the storage 130 may be connected to the processing device 120 through the network 150, as illustrated in FIG. 1, or connected to the processing device 120 directly. As still a further example, the terminal(s) 140 may be connected to the processing device 120 through the network 150, as illustrated in FIG. 1, or connected to the processing device 120 directly.

The IGRT apparatus 110 may be a multi-modality (e.g., two-modality) apparatus to acquire a medical image relating to at least one part of a subject and perform radio therapy on the at least one part of the subject. The medical image may be a computed tomography (CT) image, a magnetic resonance imaging (MRI) image, an ultrasonic image, or the like, or a combination thereof. In some embodiments, the medical image may be a two-dimensional (2D) image, a three-dimensional (3D) image, a four-dimensional (4D) image, or the like, or a combination thereof. The subject may be biological or non-biological. For example, the subject may include a patient, a man-made object, etc. As another example, the subject may include a specific portion, organ, and/or tissue of the patient. For example, the subject may include head, neck, thorax, cardiac, stomach, blood vessel, soft tissue, tumor, nodules, or the like, or a combination thereof.

In some embodiments, the IGRT apparatus 110 may include an imaging device 112, a treatment device 114, and a couch 116. The imaging device 112 may be configured to provide the medical image for determining the at least one part of the subject (e.g., an anatomical point). Exemplary imaging devices may include, for example, a CT device, a cone beam CT device, a PET device, a volume CT device, an MRI device, or the like, or a combination thereof. The treatment device 114 may be configured to perform radio therapy on the at least one part of the subject according to the medical image and other information. Exemplary treatment devices may include a linear accelerator, an X-rays treatment device, etc. The couch 116 may be configured to support and/or transfer the at least one part of the subject to for example, a scanning region of the imaging device 112 and/or the treatment device 114. For example, the couch 116 may be moved to transfer the at least one part of the subject from the imaging device 112 to the treatment device 114. In some embodiments, the couch 116 may be configured with at least one marker. The at least one marker may be detected optically, radiologically, or a combination thereof. The at least one marker may be configured to determine positions of the at least one part of the subject in an image and/or in space. In some embodiments, the imaging device 112 and the treatment device 114 may share the couch 116 in a process of image guided radio therapy (IGRT).

In some embodiments, the imaging device 112 and the treatment device 114 may be located separately from each other. In some embodiments, the imaging device 112 may be coupled with the treatment device 114. The imaging device 112 and the treatment device 114 may share a same bore which may be used to accommodate a subject to be imaged and/or treated. The couch 116 may be configured to transfer the subject to be imaged and/or treated to a detecting region in the bore. The couch 116 may include a movement assembly configured to move the couch 116 along various directions. For example, the movement assembly may extend the couch 116 along the longitudinal direction of the couch 116. As another example, the movement assembly may lift the couch 116 in the vertical direction. More descriptions of at least one portion of the IGRT apparatus 110 (e.g., the imaging device 112, the treatment device 114, the couch 116) may be found in US Publication No. 20170189719 entitled "RADIATION THERAPY POSITIONING SYSTEM.", US Publication No. 20170189720 entitled "RADIATION THERAPY SYSTEM", and/or US Publication No. 20170189724 entitled "RADIATION THERAPY SYSTEM.", the contents of which are hereby incorporated by reference. In some embodiments, the IGRT apparatus 110 may further include a positioning device. The positioning device may be configured to determine a location of at least one component of the IGRT apparatus 110, for example, the couch 116 or a marker disposed in the couch 116.

The processing device 120 may process data and/or information obtained from the IGRT apparatus 110, the storage 130, and/or the terminal(s) 140. For example, the processing device 120 may reconstruct an image relating to at least one part of a subject (e.g., a tumor) based on projection data collected by the IGRT apparatus 110 (e.g., the imaging device 112). As another example, the processing device 120 may determine a spatial position of the at least one part of the subject (e.g., a tumor) based on the image relating to the at least one part of the subject. As a further example, the processing device 120 may determine a treatment plan based on the spatial position of the at least one part of the subject (e.g., a tumor). In some embodiments, the processing device 120 may be a single server or a server group. The server group may be centralized or distributed. In some embodiments, the processing device 120 may be local or remote. For example, the processing device 120 may access information and/or data from the IGRT apparatus 110, the storage 130, and/or the terminal(s) 140 via the network 150. As another example, the processing device 120 may be directly connected to the IGRT apparatus 110, the terminal(s) 140, and/or the storage 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

The storage 130 may store data, instructions, and/or any other information. In some embodiments, the storage 130 may store data obtained from the IGRT apparatus 110, the processing device 120, and/or the terminal(s) 140. In some embodiments, the storage 130 may store data and/or instructions that the processing device 120 may execute or use to perform exemplary methods described in the present disclosure. In some embodiments, the storage 130 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform as described elsewhere in the disclosure.

In some embodiments, the storage 130 may be connected to the network 150 to communicate with one or more other components in the diagnosis and treatment system 100 (e.g., the processing device 120, the terminal(s) 140, etc.). One or more components in the diagnosis and treatment system 100 may access the data or instructions stored in the storage 130 via the network 150. In some embodiments, the storage 130 may be part of the processing device 120.

The terminal(s) 140 may be connected to and/or communicate with the IGRT apparatus 110, the processing device 120, and/or the storage 130. For example, the terminal(s) 140 may obtain a processed image from the processing device 120. As another example, the terminal(s) 140 may obtain image data acquired via the IGRT apparatus 110 and transmit the image data to the processing device 120 to be processed. In some embodiments, the terminal(s) 140 may include a mobile device 140-1, a tablet computer 140-2, a laptop computer 140-N, or the like, or any combination thereof. For example, the mobile device 140-1 may include a mobile phone, a personal digital assistance (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate exchange of information and/or data for the diagnosis and treatment system 100. In some embodiments, one or more components of the diagnosis and treatment system 100 (e.g., the IGRT apparatus 110, the processing device 120, the storage 130, the terminal(s) 140, etc.) may communicate information and/or data with one or more other components of the diagnosis and treatment system 100 via the network 150. For example, the processing device 120 may obtain image data from the IGRT apparatus 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a W-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the diagnosis and treatment system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. However, those variations and modifications do not depart the scope of the present disclosure.

Figure 2:
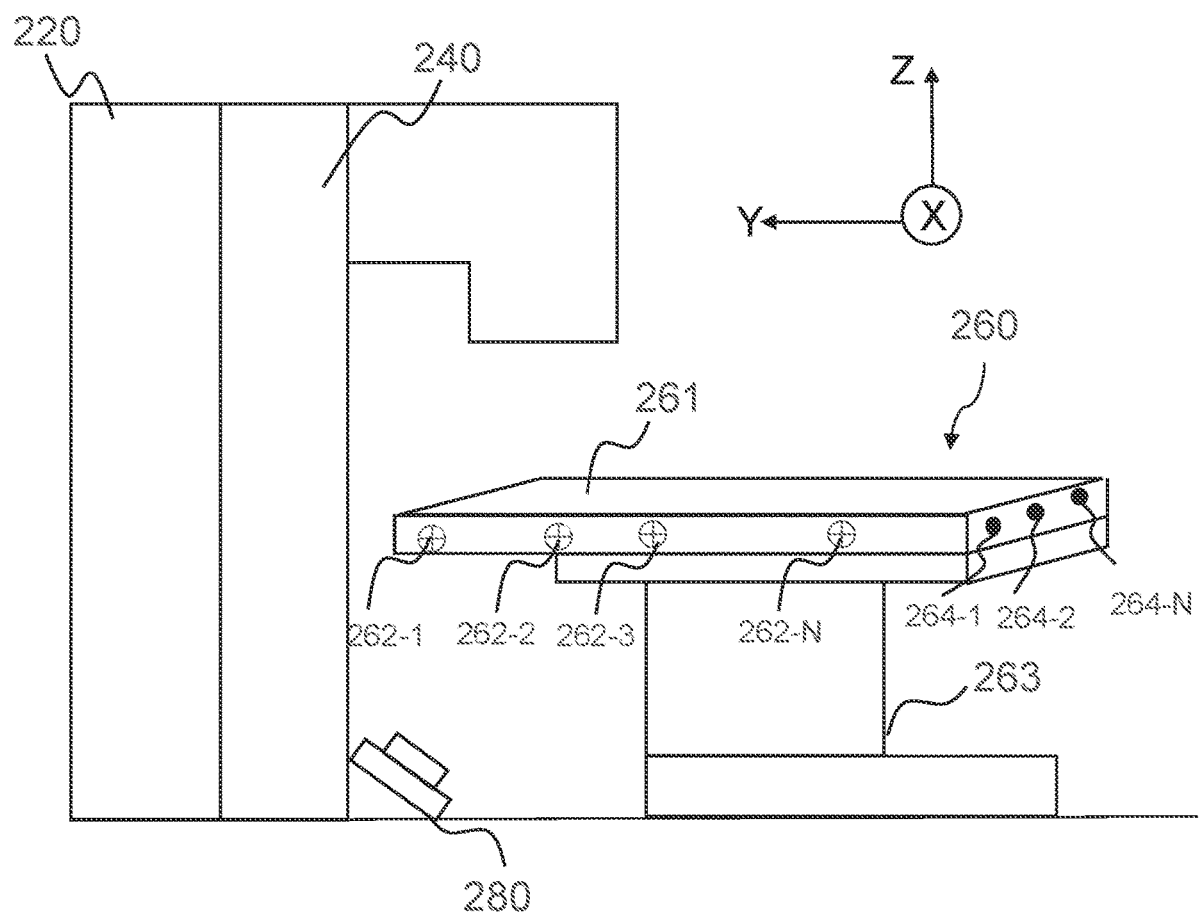
FIG. 2 illustrates a side view of an exemplary RT-CT apparatus and associated components according to some embodiments of the present disclosure.

FIG. 2 illustrates a side view of an exemplary RT-CT apparatus 200 and associated components according to some embodiments of the present disclosure. The RT-CT apparatus 200 may be the exemplary IGRT apparatus 110 as shown in FIG. 1. The RT-CT apparatus 200 may include a CT device 220, an RT device 240, a couch 260, and a positioning device 280.

The CT device 220 may acquire a CT image relating to at least one part of a subject via scanning the at least one part of the subject. In some embodiments, the CT device 220 may include a radiation source, a detector, etc. The radiation source, for example, a tube may emit radiation beams. The detector may detect the radiation beams emitted from the radiation source and generate signals (e.g., electronic signals, digital signals, etc.). The CT image may be generated based on the signals (e.g., electronic signals, digital signals, etc.). In some embodiments, the CT image may be used to identify the at least one part of the subject, classify the at least one part of the subject, diagnosis the at least one part of the subject, determine a spatial position of the at least one part of the subject, etc. For example, a spatial position of the at least one part of the subject may be determined based on a position of the at least one part of the subject represented in the CT image. In some embodiments, the position of the at least one part of the subject represented in the CT image may relate to one or more imaging parameters (also referred to as mapping parameters) of the CT device 220. As used herein, the imaging parameters of the CT device 220 may be used to convert a coordinate of a point (e.g., a target point corresponding to the at least one part of the subject) in the CT image to a spatial coordinate. The imaging parameters of the CT device 220 may include a distance from the radiation source to the detector of the of the CT device 220, a pixel size of the detector, a projection position of the radiation source on the detector, etc.

The RT device 240 may be used for treatment, for example, performing a radio therapy on the at least one part of the subject determined based on the CT image. The RT device 240 may include a cyclotron, an induction accelerator, a linear accelerator (LINAC), etc. In some embodiments, the CT device 220 and the RT device 240 may be set back to back or adjacent to each other as illustrated in FIG. 2. The CT device 220 and the RT device 240 may have a same rotation axis. Specifically, the CT device 220 may be connected to the RT device 240. In some embodiments, the CT device 220 and the RT device 240 may be set separately from each other. In some embodiments, the CT device 220 and the RT device 240 may be mounted and/or fixed on the ground. In some embodiments, the CT device 220 and/or the RT device 240 may be moveable. For example, the CT device 220 and/or the RT device 240 may be moved using a moveable device (e.g., a trolley or wheels) mounted on the CT device 220 and/or the RT device 240.

The couch 260 may be configured to support and/or transfer the at least one part of the subject. The couch 260 may be moved from a first position to a second position. For example, the couch 260 may be moved to transfer the at least one part of the subject from a position where the CT device 220 is located to a position where the RT device 240 is located. In some embodiments, the couch 260 may be moved using a moveable device (e.g., a trolley or wheels) mounted on the couch 260.

The couch 260 may include a table top 261, a supporting assembly 263, or the like, or a combination thereof. The supporting assembly 263 may support the table top 261. In some embodiments, the table top 261 may be extendable along the longitudinal direction of the couch 260 such that the at least one part of the subject may be transferred to for example, a scanning region of the CT device 220 and/or the treatment position of the RT device 240.

The couch 260 may further include a marker. The marker may include a radiologically detectable marker, an optically detectable marker, or a marker that is both radiologically and optically detectable. As user herein, a radiologically detectable marker may refer to a marker that may be penetrated and/or detected by radiation rays (e.g., X rays, γ rays, etc.). An optically detectable marker may refer to a marker that may reflect light. A radiologically and optically detectable marker may refer to a marker that may be penetrated and/or detected by radiation rays (e.g., X rays, γ rays, etc.) and reflect light. In some embodiments, the couch 260 may include one or more groups of markers (e.g., a first group of markers including a first marker 262-1, a first marker 262-2, . . . , a first marker 262-N and/or a second group of markers including a second marker 264-1, a second marker 264-2, . . . , a second marker 264-N). In some embodiments, a marker in the first group may be a radiologically detectable marker that may be detected by radiation rays (e.g., X rays, γ rays, etc.). A marker in the second group of markers may be an optically detectable marker that may be detected by visible light. In some embodiments, at least one portion of the couch may be designated as an optically detectable marker. For example, the at least one portion of the couch may be signed by, for example, a specific symbol (e.g., a circular) to be a marker.

The marker may include a specification defined by one or more parameters including a shape, a size, a color, a material, or the like, or a combination thereof. The shape may include a sphere, an ellipsoid, a cube, a wire, or other shapes. The material may include a metal material, a resin material, a ceramic material, etc. In some embodiments, the density of the material may be greater than water. In some embodiments, markers in the first group or the second group may be in different specifications such that each of the markers in the first group or the second group may be distinguished from each other. For example, the first marker 262-1 and the first marker 262-2 may have shapes of a sphere and a cube respectively, such that the first marker 262-1 may be distinguished with the first marker 262-2.

The marker may be disposed at a suitable position of the couch 260. In some embodiments, the first group of markers and the second group of markers may be disposed inside of the table top 261. Markers in the first group and/or the second group may be arranged inside of the table top 261 in multiple rows along the longitudinal direction of the couch 260. Each of the multiple rows of the markers may include at least one marker. In some embodiments, a row of markers in the first group and a row of markers in the second group may be arranged adjoining with each other. In some embodiments, the first group of markers may be disposed inside of the table top 261. The second group of markers may be disposed on the bottom of the table top 261, a side of the table top 261, or any other position of the couch 260 (e.g., a base of the couch 260) that may be detected by, for example, the positioning device 280.

The positioning device 280 may be configured to position a component (e.g., the marker, the couch 260, etc.) of the RT-CT apparatus 200 by collecting data relating to movements and/or positions of the component (e.g., the marker, the couch 260, etc.). The data relating to a motion and/or position of a component in the RT-CT apparatus 200 may be used to estimate the spatial position of a component in the RT-CT apparatus 200. The data relating to a motion and/or position of a component (e.g., the marker, the couch 260, etc.) in the RT-CT apparatus 200 may include movement data (e.g., a speed, a displacement, an acceleration, etc.), image data (e.g., an image), or other data relating to a position of the component (e.g., the marker, the couch 260, etc.) of the RT-CT apparatus 200.

The positioning device 280 may include a sensor, a camera, a rangefinder, or the like, or a combination thereof. Exemplary sensors may include a speed sensor, an acceleration sensor, a displacement sensor, or the like, or a combination thereof. Exemplary rangefinders may include a laser rangefinder, an ultrasonic rangefinder, an electromagnetic rangefinder, etc. Exemplary cameras may include applying a photoelectric sensor, for example, a charge coupled device (CCD) photoelectric sensor, a CMOS photoelectric sensor, etc. The sensor (e.g., a speed sensor, an acceleration sensor, a displacement sensor, etc.) may collect the movement data relating to a component (e.g., the marker, the couch 260, etc.) of the RT-CT apparatus 200. The camera may collect an optical image of a component (e.g., the marker, the couch 260, etc.) of the RT-CT apparatus 200.

The positioning device 280 may be disposed at a suitable position in the space accommodating the RT-CT apparatus 200. In some embodiments, the positioning device 280 may be coupled to the couch 260. For example, a sensor (e.g., a speed sensor, an acceleration sensor, a displacement sensor, etc.) may be coupled to the marker (e.g., the first marker 262-1, the first marker 262-2, the first marker 262-3, . . . , the first marker 262-N, the second marker 264-1 the second marker 264-2, . . . , and/or the second marker 264-N). In some embodiments, the positioning device 280 may be disposed at a position relative to the couch 260. For example, a camera may be disposed at a base of the RT device 240.

In some embodiments, a spatial position of, for example, a component of the RT-CT apparatus 200 or at least one part of a subject may be defined by a coordinate system. Exemplary coordinate systems may include a space rectangular coordinate system, a spherical coordinate system, a camera coordinate system, or the like, or a combination thereof. A coordinate origin of the coordinate system may be variable. In some embodiments, the coordinate origin of the coordinate system may be set at an isocenter of the CT device 220, an isocenter of the RT device 240, or any other suitable position. As used herein, the isocenter the CT device 220 (or the RT device 240) may refer to an intersection of a rotation axis of the CT device 220 (or the RT device 240), a central axis of a radiation source of the CT device 220 (or the RT device 240), and a rotation axis of the couch 260. In some embodiments, components of the RT-CT apparatus 200 (e.g., the CT device 220, the RT device 240, the couch 260, and/or the positioning device 280) may share one single coordinate system as illustrated in FIG. 200. For example, the single coordinate system may have an X axis, a Y axis, and a Z axis. In some embodiments, the Y axis may be parallel with a longitudinal axis of the couch 260. The Z axis and the Y axis may be in a vertical plane, the X axis and the Y axis may be in a horizontal plane. In some embodiments, the CT device 220 may be assigned with a first coordinate system, and the RT device 240 may be assigned with a second coordinate system. The first coordinate system and the second coordinate system may be converted with each other based on, for example, a position relationship of a first coordinate origin of the first coordinate system and a second coordinate origin of the second coordinate system.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the RT-CT apparatus 200 may further include an imaging device, such as a PET device, a MRI device, etc. As another example, the positioning device 280 may be assigned with a third coordinate system.

FIG. 3 is a schematic diagram illustrating exemplary hardware and/or software components of an exemplary computing device 300 on which the processing device 120 may be implemented according to some embodiments of the present disclosure. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data obtained from the IGRT apparatus 110, the storage 130, terminal(s) 140, and/or any other component of the diagnosis and treatment system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors, thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the IGRT apparatus 110, the storage 130, the terminal(s) 140, and/or any other component of the diagnosis and treatment system 100. In some embodiments, the storage 320 may include a mass storage, a removable storage, a volatile read-and-write memory, a read-only memory (ROM), or the like, or a combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for the processing device 120 for determining a target flip angle schedule.

The I/O 330 may input and/or output signals, data, information, etc. In some embodiments, the I/O 330 may enable a user interaction with the processing device 120. In some embodiments, the I/O 330 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 340 may be connected to a network (e.g., the network 150) to facilitate data communications. The communication port 340 may establish connections between the processing device 120 and the IGRT apparatus 110, the storage 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
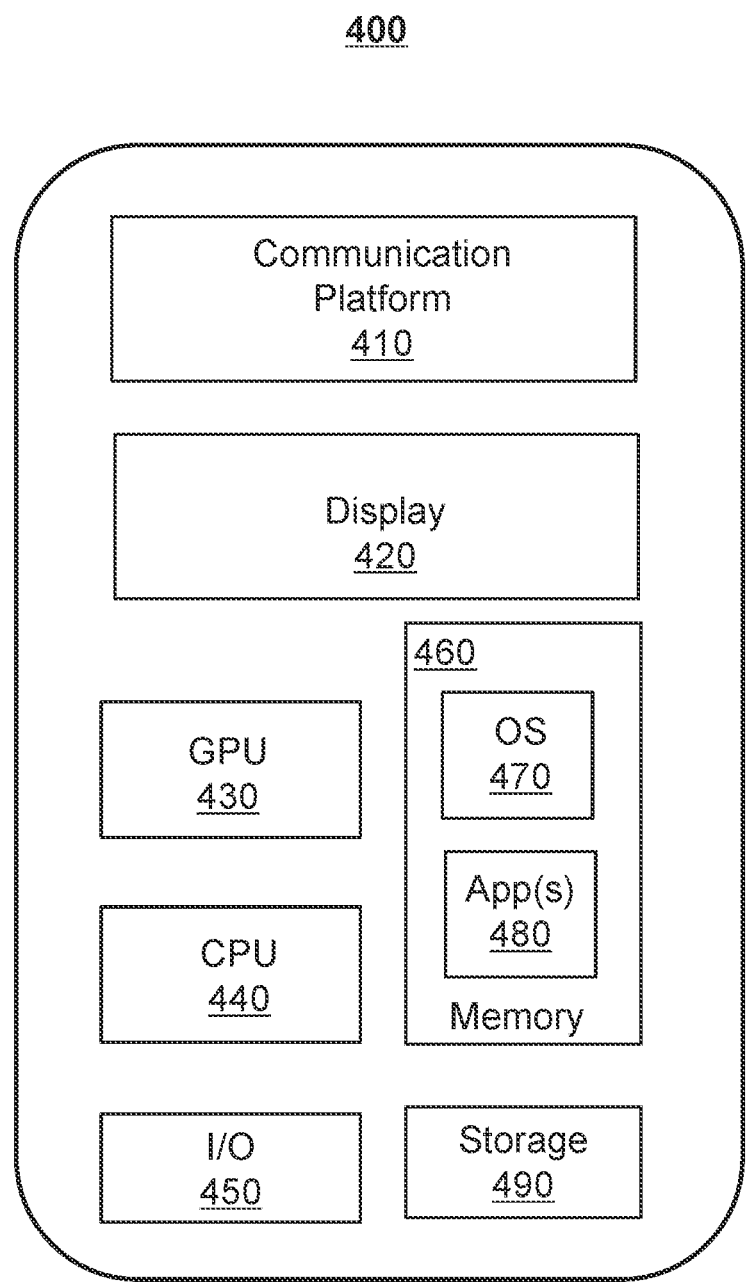
FIG. 4 is a schematic diagram illustrating exemplary hardware and/or software components of an exemplary mobile device on which the terminal(s) may be implemented according to some embodiments of the present disclosure.

FIG. 4 is a schematic diagram illustrating exemplary hardware and/or software components of an exemplary mobile device 400 on which the terminal(s) 140 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 120. User interactions with the information stream may be achieved via the I/O 450 and provided to the processing device 120 and/or other components of the diagnosis and treatment system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
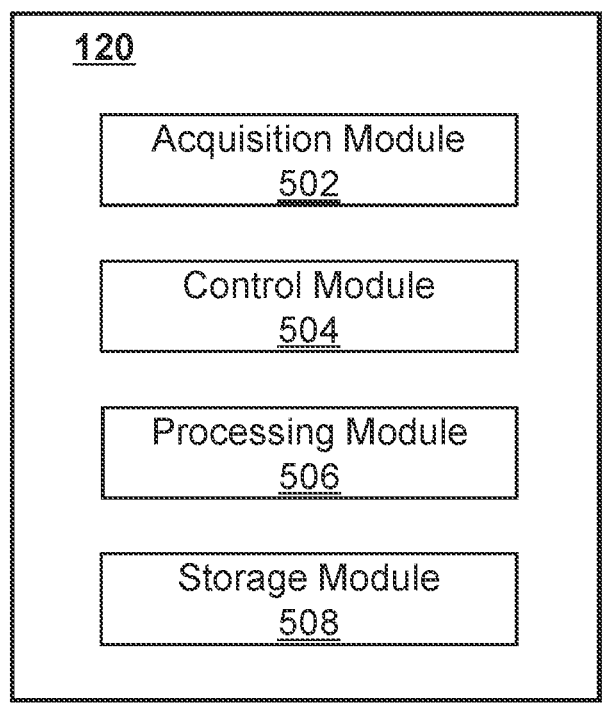
FIG. 5 is a block diagram illustrating an exemplary processing device according to some embodiments of the present disclosure.

FIG. 5 is a block diagram illustrating an exemplary processing device 120 according to some embodiments of the present disclosure. The processing device 120 may include an acquisition module 502, a control module 504, a processing module 506, and a storage module 508. At least a portion of the processing device 120 may be implemented on a computing device as illustrated in FIG. 3 or a mobile device as illustrated in FIG. 4.

The acquisition module 502 may acquire data. In some embodiments, the data may be acquired from the IGRT apparatus 110, the storage 130, and/or the terminal(s) 140. In some embodiments, the data may include image data (e.g., a radiological image, an optical image, etc.), motion or position data (e.g., a speed, a displacement, a spatial position, etc.) relating to a component in the IGRT apparatus 110, instructions, or the like, or a combination thereof. The instructions may be executed by the processor(s) of the processing device 120 to perform exemplary methods described in the present disclosure. In some embodiments, the acquired data may be transmitted to the processing module 506 for further processing, or stored in the storage module 508.

The control module 504 may control operations of the acquisition module 502, the processing module 506, and/or the storage module 508, for example, by generating one or more control parameters. For example, the control module 504 may control the processing module 506 to determine a spatial position of at least one part of a subject and/or a component of the IGRT apparatus 110. As another example, the control module 504 may control the acquisition module 502 to acquire image data (e.g., a radiological image, an optical image, etc.) from the imaging device 112 of the IGRT apparatus 110. In some embodiments, the control module 504 may receive a real-time command or retrieve a predetermined instruction provided by a user (e.g., a doctor) to control one or more operations of the acquisition module 502 and/or the processing module 506. For example, the control module 504 may adjust the acquisition module 502 and/or the processing module 506 to generate image data (e.g., an image) according to the real-time instruction and/or the predetermined instruction. In some embodiments, the control module 504 may communicate with one or more other modules of the processing device 120 for exchanging information and/or data.

The processing module 506 may process data provided by various modules of the processing device 120. In some embodiments, the processing module 506 may process a radiological image relating to at least one part of a subject to determine a spatial position of the at least one part of the subject. In some embodiments, the processing module 506 may determine a spatial position of a component of the IGRT apparatus 110 (e.g., the couch 116, the marker, etc.) based on data relating to a motion or position of a component of the IGRT apparatus 110 collected by the positioning device 280.

The storage module 508 may store information. The information may include programs, software, algorithms, data, text, number, images and some other information. For example, the information may include image data (e.g., a radiological image, an optical image, etc.), motion or position data (e.g., a speed, a displacement, an acceleration, a spatial position, etc.) relating to a component in the IGRT apparatus 110 (e.g., the couch 116), instructions, or the like, or a combination thereof. In some embodiments, the storage module 508 may store program(s) and/or instruction(s) that can be executed by the processor(s) of the processing device 120 to acquire data, determine a spatial position of at least one part of a subject.

Figure 6:
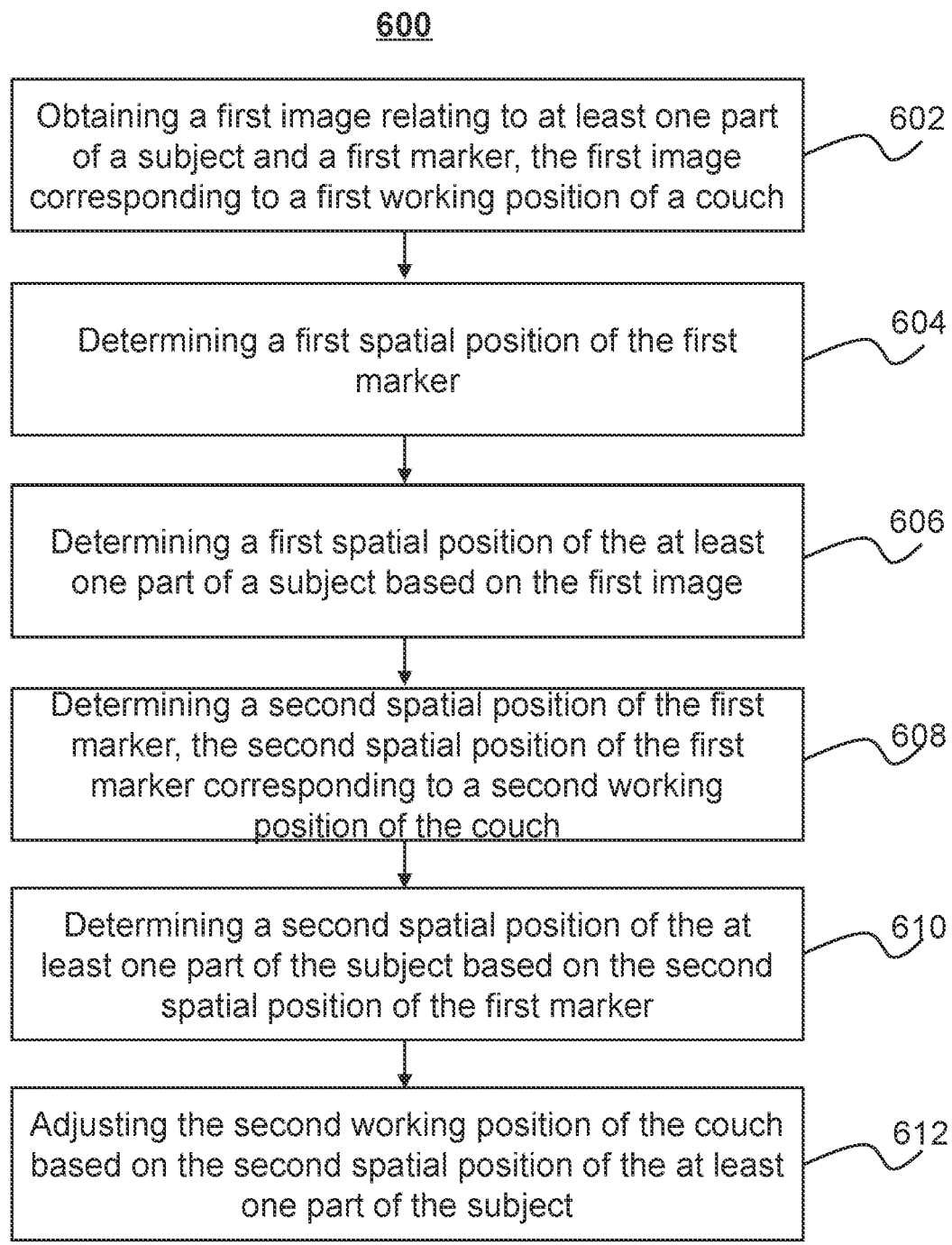
FIG. 6 is a flowchart illustrating an exemplary process for determining a spatial position of at least one part of a subject at a treatment position according to some embodiments of the present disclosure.

In some embodiments, one or more modules illustrated in FIG. 5 may be implemented in at least part of the diagnosis and treatment system 100 as illustrated in FIG. 1. For example, the acquisition module 502, the control module 504, the processing module 506, and/or the storage module 508 may be integrated into a console (not shown). Via the console, a user may set parameters for scanning a subject, controlling imaging processes, controlling parameters for reconstruction of an image, etc. In some embodiments, the console may be implemented via the processing device 120 and/or the terminal(s) 140, FIG. 6 is a flowchart illustrating an exemplary process 600 for determining a spatial position of at least one part of a subject at a treatment position according to some embodiments of the present disclosure. In some embodiments, one or more operations of process 600 illustrated in FIG. 6 may be implemented in the diagnosis and treatment system 100 illustrated in FIG. 1. For example, the process 600 illustrated in FIG. 6 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

In 602, a first image relating to at least one part of a subject and a first marker may be obtained and the first image may correspond to a first working position of a couch. Operation 602 may be performed by the acquisition module 502. The first image may be acquired by an imaging device (e.g., the CT device 220) of a medical device (e.g., the RT-CT apparatus 200) via scanning the at least one part of the subject when the couch is at the first working position (e.g., a position where the CT device 220 is located). The first image may include a radiological image, for example, a CT image, an MR image, an X-rays image, a PET image, or the like, or a combination thereof.

In some embodiments, the first marker may include a radiologically detectable marker that may be detected radiologically. In some embodiments, the first marker may include a radiologically and optically detectable marker as described elsewhere in the present disclosure. See, for example FIG. 2, and description thereof.

The first marker (e.g., the first marker 262-1, the first marker 262-2, the first marker 262-3, . . . , the first marker 262-N) may be represented in the first image as a reference point. The at least one part of the subject may be represented in the first image as a target point. As used herein, the term "point" represented in the first image may refer to a region including one or more pixels or voxels in the first image. Positions of the reference point corresponding to the first marker and the target point corresponding to the at least one part of the subject in the first image may be denoted by a first coordinate system applied to the first image. For example, the position of the first reference point or the target point in the first image may be denoted by a coordinate of a pixel or a voxel located at the center of the first reference point or the target point.

In 604, a first spatial position of the first marker may be determined. In some embodiments, operation 604 may be performed by the acquisition module 502 or the processing module. As used herein, the first spatial position may refer to a location of an object (e.g., the first marker 262-1, the first marker 262-2, . . . , the first marker 262-N, the at least one part of the subject, etc.) in space (e.g., the space where the medical device is located in) when the couch is located at the first working position (e.g., a position where the imaging device 112 is located).

The first spatial position of the first marker may be denoted by a second coordinate system applied to a component (e.g., the CT device 220, the RT device 240, etc.) of the medical device (e.g., the RT-CT apparatus 200). For example, the first spatial position of the first marker may be denoted by a three-dimension coordinate corresponding to the second coordinate system. A coordinate origin of the second coordinate system may be variable. For example, the second coordinate system may have a coordinate origin of an isocenter of the imaging device (e.g., the CT device 220) of the medical device (e.g., the RT-CT apparatus 200). As another example, the second coordinate system may have a coordinate origin of an isocenter of a treatment device (e.g., the RT device 240) of the medical device (e.g., the RT-CT apparatus 200). As a still example, the coordinate origin of the second coordinate system may set at any suitable position in the space accommodating the medical device (e.g., the RT-CT apparatus 200). In some embodiments, the second coordinate system may be set by a user via the terminal(s) 140 or according to a default setting of the diagnosis and treatment system 100.

In some embodiments, the first spatial position of the first marker may be determined based on a distance and direction from the first marker disposed on the couch to the coordinate origin of the second coordinate system (e.g., the isocenter of the imaging device (e.g., the CT device 220). In some other embodiments, the distance and direction from the first marker to the coordinate origin of the second coordinate system may be obtained from a prior measurement. For example, the information regarding the distance and direction from the first marker to the coordinate origin of the second coordinate system may be retrieved from a storage (e.g., the storage 130, the storage module 508, etc.). In some embodiments, the first spatial position of the first marker may be obtained from a prior measurement directly. For example, the information (e.g., a three-dimension coordinate) regarding the first spatial position may be retrieved from a storage (e.g., the storage 130, the storage module 508, etc.).

In some embodiments, the determination of the first spatial position of the first marker may include determining and/or identifying the first marker from the first image based on the first reference point. For example, the couch may be configured with multiple markers (e.g., the first marker 262-1, the first marker 262-2, . . . , the first marker 262-N) in different specifications (e.g., shapes, materials, etc.). The first marker may be identified from the multiple markers based on the first reference point in the first image and the specification of the first marker. Then, the first spatial position of the first marker may be determined.

In 606, a first spatial position of the at least one part of the subject may be determined based on the first image. Operation 606 may be performed by the processing module 506. In some embodiments, the first spatial position of the at least one part of the subject may be denoted by the second coordinate system applied to the medical device applied to a component (e.g., the CT device 220, the RT device 240, etc.) of the medical device (e.g., the RT-CT apparatus 200). For example, the first spatial position of the at least one part of the subject may be denoted by a three-dimension coordinate corresponding to the second coordinate system.

Figure 7:
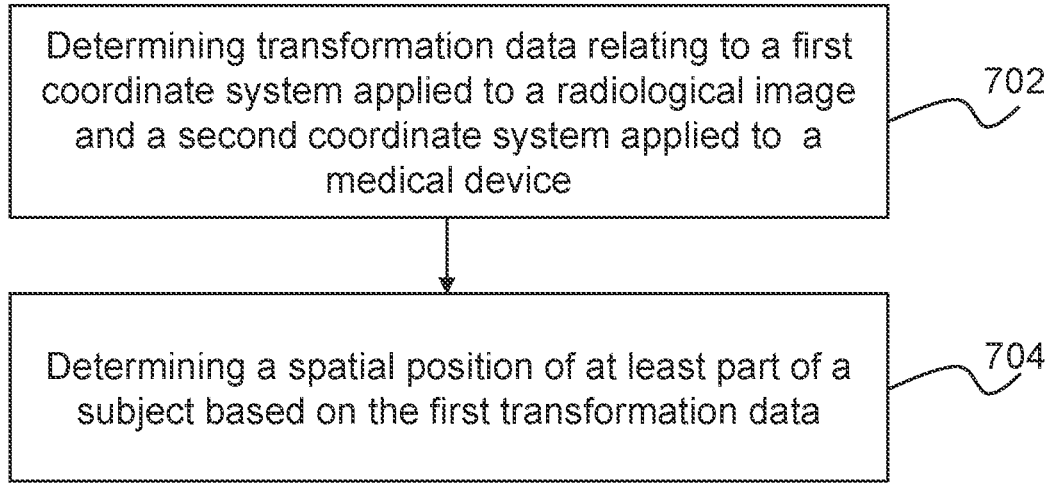
FIG. 7 is a flowchart illustrating an exemplary process for determining a spatial position of at least one part of a subject at an imaging position according to some embodiments of the present disclosure.

In some embodiments, the first spatial position of the at least one part of the subject may be determined based on a first transformation between the first coordinate system and the second coordinate system according to process 700 as described in FIG. 7. For example, a coordinate of the target point corresponding to the at least one part of the subject may be converted to the three-dimension coordinate of the at least one part of the subject based on the first transformation between the first coordinate system and the second coordinate system. As another example, a spatial position relationship between the first marker and the at least one part of the subject may relate to a position relationship between the reference point corresponding to the first marker and the target point corresponding to the at least one part of the subject represented in the first image. Furthermore, the spatial position relationship between the first marker and the at least one part of the subject may be determined by converting the position relationship between the reference point and the target point based on the first transformation between the first coordinate system and the second coordinate system. Then, the first spatial position of the at least one part of the subject may be determined based on the spatial position relationship between the first marker and the at least one part of the subject and the first spatial position of the first marker.

In 608, a second spatial position of the first marker may be determined. Operation 608 may be performed by the processing module 506. As used herein, the second spatial position may refer to a location of an object (e.g., the first marker, the at least one part of the subject, etc.) in space (e.g., the space where the medical device is located in) when the couch is located at a second working position (e.g., a position where the treatment device 116 is located). In some embodiments, the second spatial position of the first marker may be denoted by the second coordinate system applied to the medical device.

In some embodiments, the second spatial position of the first marker may be determined based on data relating to the first marker acquired by a positioning device (e.g., the positioning device 280 as illustrated in FIG. 2). In some embodiments, the data relating to the first marker may include an optical image relating to the first marker acquired by the positioning device (e.g., a camera). The second spatial position of the first marker may be determined based on the optical image and a second transformation between a third coordinate system applied to the positioning device and a fourth coordinate system applied to the optical image relating to the first marker. The second transformation between the third coordinate system applied to the positioning device and the fourth coordinate system applied to the optical image may include transformation data (e.g., a transformation equation or algorithm) determined based on a camera calibration. The camera calibration may be obtained from a prior measurement. For example, the information regarding the camera calibration may be retrieved from a storage (e.g., the storage 130, the storage module 508, etc.). The second spatial position of the first marker determined based on the second transformation between the third coordinate system and the fourth coordinate system may be denoted by the third coordinate system. Then, the second spatial position of the first marker denoted by the second coordinate system may be determined based on a third transformation between the third coordinate system and the second coordinate system. The third transformation may be obtained from a prior measurement. For example, the information regarding the third transformation may be retrieved from a storage (e.g., the storage 130, the storage module 508, etc.).

In some embodiments, the data relating to the first marker may include movement data of the first marker detected by the positioning device (e.g., a displacement sensor, a speed sensor, an acceleration sensor, a range finder (e.g., a laser interferometer, an ultrasonic range finder, etc.), etc.). The movement data of the first marker may include, for example, a displacement of the first marker, a speed of the first marker, an acceleration of the first marker, a movement direction of the first marker, etc. As used herein, the displacement of the first marker may refer to a location change in space when the couch moves from the first working position to the second working position. The second spatial position of the first marker may be determined based on the displacement of the first marker. In some embodiments, the displacement of the first marker may be acquired from the positioning device directly. In some embodiments, the displacement of the first marker may be determined based on other movement data (e.g., the speed of the first marker, the acceleration of the first marker, the movement direction of the first marker, etc.) by the processing module 506. For example, the acceleration of the first marker may be acquired by the positioning device (e.g., an acceleration sensor). The processing module 506 may process the acceleration of the first marker by performing a double integral on the acceleration of the first marker to determine the displacement of the first marker. As another example, the displacement of the first marker may be determined based on a laser triangulation algorithm. Furthermore, the positioning device (e.g., a laser interferometer) may emit a laser to the couch, and the couch may reflect the laser to the positioning device (e.g., a laser interferometer). The displacement of the first marker may be determined based on the reflected laser and the emitting laser by using the laser triangulation algorithm.

In some embodiments, the second spatial position of the first marker may be determined based on a second marker disposed in the couch relative to the first marker. In some embodiments, a first spatial position of the second marker may be obtained from, for example, a prior measurement. For example, the information regarding first spatial position of the second marker may be retrieved from a storage (e.g., the storage 130, the storage module 508, etc.). A second spatial position of the second marker may be determined based on data relating to a motion and/or position of the second marker. Then, the second spatial position of the first marker may be determined based on the second spatial position of the second marker, the first spatial position of the first marker, and the first spatial position of the second marker as described in connection with FIG. 8.

In 610, a second spatial position of the at least one part of the subject may be determined based on the second spatial position of the first marker and the first spatial position of the at least one part of the subject. Operation 610 may be performed by the processing module 506. In some embodiments, when the couch moves from the first working position to the second working position, a position relationship between the first marker and the at least one part of the subject may be unchanged. The position relationship may be determined based on the first spatial position of the first marker and the first spatial position of the at least one part of the subject determined in operation 604 and operation 606, respectively. The second spatial position of the at least one part of the subject may be determined based on the position relationship between the first marker and the at least one part of the subject and the second spatial position of the first marker determined in operation 608.

In 612, the second working position of the couch may be adjusted based on the second spatial position of the at least one part of the subject. Operation 612 may be performed by the processing module 506. In some embodiments, the second working position of the couch may be adjusted to align the at least one part of the subject with an isocenter of the treatment device (e.g., the RT device 240) of the medical device (e.g., the RT-CT device 200). For example, when the couch moves from the first working position to the second working position (e.g., from the imaging device to the treatment device), the couch may deflect or sag. The sag of the couch may be related to a difference between the first spatial position of the at least one part of the subject and the second spatial position of at least one part of the subject on a vertical direction (e.g., the Z axis illustrated in FIG. 2). The couch may be raised up or lowered down based on the difference between the first spatial position of the at least one part of the subject and the second spatial position of at least one part of the subject on the vertical direction (e.g., the Z axis illustrated in FIG. 2). Thus, the at least one part of the subject may be aligned with the isocenter of the treatment device (e.g., the RT device 240).

In some embodiments, operations 606 and 610 may be omitted and a position relationship between the at least one part of the subject and an isocenter of the second device when the couch is at the second working position may be determined based on at least one of the first spatial position or the second spatial position. The second working position of the couch may be adjusted based on the position relationship between the at least one part of the subject and an isocenter of the second device when the couch is at the second working position. For example, a position relationship between the at least one part of the subject and an isocenter of the first device when the couch is at the first working position may be determined based on the first image, and the position relationship between the at least one part of the subject and the isocenter of the second device may be determined based on the position relationship between the at least one part of the subject and the isocenter of the first device. As another example, a position relationship between the first marker and the at least one part of the subject may be determined based on the first image. A position relationship between the isocenter of the second device and the second spatial position of the first marker may be determined; and the position relationship between the isocenter of the second device and the at least one part of the subject when the couch is at the second working position may be determined based on the position relationship between the isocenter of the second device and the second spatial position of the first marker and the position relationship between the first marker and the at least one part of the subject.

In some embodiments, when the couch is at the first working position, a position relationship between the at least a part of the subject and the isocenter of the first device may be determined based on the first image. For example, the first spatial position of the at least a part of the subject may be determined in operation 606 based on the first image. The spatial position of the isocenter of the first device may be a default setting of the system. The position relationship between the at least a part of the subject and the isocenter of the first device may be determined based on the first spatial position of the at least a part of the subject and the spatial position of the isocenter of the first device. As another example, the first spatial position of the first marker may be determined in operation 606 based on the first image. The position relationship between the first marker and the at least a part of the subject may be determined based on a position relationship between the target point representing the at last a part of the subject and the first reference point representing the first marker in the first image. A position relationship between the first spatial position of the first marker and the isocenter of the first device may be determined based on the first spatial position of the first marker and the spatial position of the isocenter of the first device. Then the position relationship between the at least a part of the subject and the isocenter of the first device may be determined based on the position relationship between the first marker and the isocenter of the first device and the position relationship between the first marker and the at least a part of the subject. Further, the position relationship between the first spatial position of the first marker and the isocenter of the first device may be denoted as a first vector and the position relationship between the first marker and the at least a part of the subject may be denoted as a second vector, the position relationship between the at least a part of the subject and the isocenter of the first device may be determined based on a difference between the first vector and the second vector.

When the couch moves to the second working position, the second spatial position of the first marker may be determined as described in operation 608. When the couch moves to the second working position, the couch loaded with the subject (e.g., a patient) may sag or deflect, and the position relationship between the at least a part of the subject and the isocenter of the second device may be changed or different from the position relationship between the at least a part of the subject and the isocenter of the first device.

In some embodiments, the position relationship between the at least a part of the subject and the isocenter of the second device may be determined based on the position relationship between the at least a part of the subject and the isocenter of the first device and the deformation measurement of the couch at the second working position with respect to the first working position. The deformation measurement of the couch at the second working position with respect to the first working position may be determined based on a difference between the first spatial position and the second spatial position. For example, the deformation measurement of the couch at the second working position with respect to the first working position may be determined based on the difference between the second working position with respect to the first working position in a vertical direction. For example, the position relationship between the at least a part of the subject and the isocenter of the first device may be denoted as a third vector and the deformation measurement of the couch at the second working position with respect to the first working position may be denoted as a fourth vector, the position relationship between the at least a part of the subject and the isocenter of the second device may be determined based on a sum of the third vector and the fourth vector.

In some embodiments, the position relationship between the at least a part of the subject and the isocenter of the second device may be determined based on the position relationship between the at least a part of the subject and the second spatial position of the first marker and a position relationship between the second spatial position of the first marker and the spatial position of the isocenter of the second device. For example, the position relationship between the second spatial position of the first marker and the at least a part of the subject may be the same as or similar to the position relationship between the at least a part of the subject and the first spatial position of the first marker and may be denoted as the second vector. The position relationship between the second spatial position of the first marker and the spatial position of the isocenter of the second device may be denoted as a fifth vector, and the position relationship between the at least a part of the subject and the isocenter of the second device may be determined based on a difference between the fifth vector and the second vector.

The displacement measurement of the couch may be determined based on the position relationship between the at least a part of the subject and the isocenter of the second device such that the at least a part of the subject may be moved to the isocenter of the second device based on the displacement measurement of the couch. For example, the position relationship between the at least a part of the subject and the isocenter of the second device may be denoted as a target vector, and the target vector may be designated as the displacement measurement of the couch.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 604 may be unnecessary. As another example, operations 602 and 604 may be performed simultaneously.

FIG. 7 is a flowchart illustrating an exemplary process 700 for determining a spatial position of at least one part of a subject at an imaging position according to some embodiments of the present disclosure. In some embodiments, one or more operations of process 700 illustrated in FIG. 7 may be implemented in the diagnosis and treatment system 100 illustrated in FIG. 1. For example, the process 700 illustrated in FIG. 7 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). Operation 606 may be performed according to process 700.

In 702, a transformation data relating to a first coordinate system applied to a radiological image and a second coordinate system applied to a medical device (e.g., the RT-CT apparatus 200) may be determined. Operation 702 may be performed by the processing module 506. The medical device (e.g., the RT-CT apparatus 200) may be configured to acquire a medical image and perform radio therapy. The medical device (e.g., the RT-CT apparatus 200) may include an imaging device (e.g., the CT device 220) and a treatment device (e.g., the RT device 240) as described elsewhere in the present disclosure. See, for example, FIG. 2 and description thereof. The radiological image may be obtained from the medical device (e.g., the CT device 220) as described in connection with 602 as illustrated in FIG. 6.

The first coordinate system and the second coordinate system may be set by a user via the terminal(s) 140 or according to a default setting of the diagnosis and treatment system 100. Information regarding the first coordinate system and the second coordinate system may be retrieved from a storage (e.g., the storage 130, the storage module 508, etc.). For example, a coordinate origin of the first coordinate system and/or a coordinate origin of the second coordinate system may be set at a center of the radiological image and an isocenter of the medical device automatically. As another example, the coordinate origin of the first coordinate system and/or the coordinate origin of the second coordinate system may be set at any suitable position by a user.

The transformation data may be used to perform a conversion between the first coordinate system and the second coordinate system. Furthermore, the conversion between the first coordinate system and the second coordinate system may include a conversion between a spatial coordinate of an object (e.g., the first marker, the at least one part of the subject) defined by the second coordinate system and a coordinate of a point in the radiological image defined by the first coordinate system. The transformation data relating to the first coordinate system and the second coordinate system may include a transformation relationship between the first coordinate system and the second coordinate system. In some embodiments, the transformation relationship may be represented by, for example, a transformation equation or algorithm. The transformation relationship (e.g., a transformation equation or algorithm) may be defined by one or more imaging parameters (also referred to as mapping parameters) relating to the imaging device (e.g., the CT device 220) of the medical device as described elsewhere in the present disclosure. For example, the imaging parameters relating to the imaging device may include a distance from a radiation source of the imaging device to a detector of the imaging device, a pixel size of the detector in the imaging device, a projection position of the radiation source on the detector of the imaging device, etc. Furthermore, the first marker and/or the at least one part of the subject may be projected to a plane (also referred to as a projection plane) corresponding to the radiological image. Projection positions of the first marker and/or the at least one part of the subject on the projection plane corresponding to the radiological image may relate to the imaging parameters relating to the imaging device and the first spatial positions of the first marker and/or the at least one part of the subject. Thus, the first spatial positions of the at least one part of the subject may be determined based on the imaging parameters relating to the imaging device.

In some embodiments, the imaging parameters may be determined by calibrating the imaging device based on a calibration model. Exemplary calibration models may include a pinhole camera model, a two plane correction model, a Faugeras correction model, or the like, or a combination thereof. In some embodiments, the imaging parameters may be obtained from the storage 130, storage module 508, the terminal(s) 140, or any other external storage.

In 704, a spatial position of at least one part of a subject may be determined based on the transformation data. Operation 704 may be performed by the processing module 506. The spatial position of the at least one part of the subject may be denoted by a second coordinate corresponding to the second coordinate system. The at least one part of the subject may be represented in the radiological image as a target point. As used herein, the term "point" may refer to a region including one or more pixels or voxels in the radiological image. A position of the target point in the radiological image may be denoted by a first coordinate corresponding to the first coordinate system. The second coordinate of the at least one part of the subject may be determined by converting the first coordinate of the target point based on the transformation data.

In some embodiments, the radiological image may include a reference point corresponding to a marker (e.g., the first marker 262-1, the first marker 262-2, the first marker 262-3, . . . , and/or the first marker 262-N) as described elsewhere in the present disclosure. See, for example, FIG. 2 and description thereof. A spatial position of the marker may be determined as described in connection with operation 604. The spatial position of the at least one part of the subject may be determined based on the spatial position of the marker and the transformation data. Furthermore, a spatial position relationship between the at least one part of the subject and the marker may be determined based on the transformation data and a position relationship between the target point corresponding to the at least one part of the subject and the reference point corresponding to the marker. Then, the spatial position of the at least one part of the subject may be determined based on the spatial position of the marker and the spatial position relationship between the at least one part of the subject and the marker.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, process 700 may include establishing the first coordinate system and/or the second coordinate system.

Figure 8:
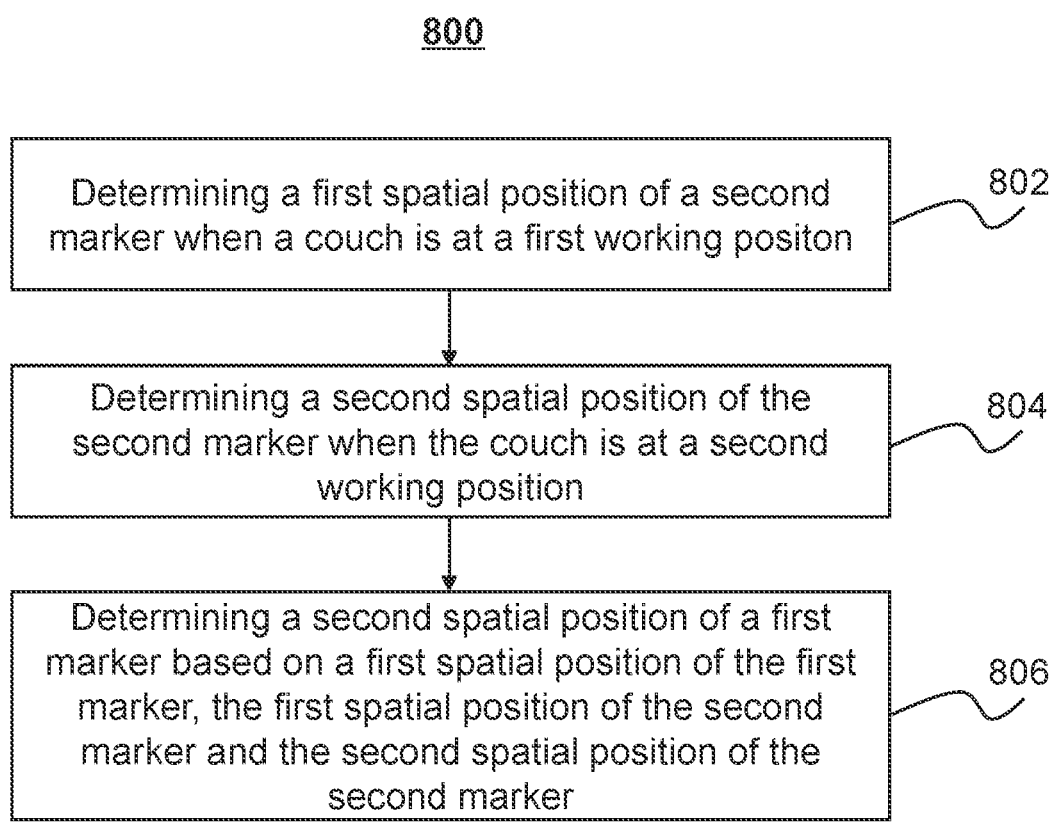
FIG. 8 is a flowchart illustrating an exemplary process for determining a spatial position of a marker at a treatment position according to some embodiments of the present disclosure.

FIG. 8 is a flowchart illustrating an exemplary process 800 for determining a spatial position of a marker at a treatment position according to some embodiments of the present disclosure. In some embodiments, one or more operations of process 800 illustrated in FIG. 8 may be implemented in the diagnosis and treatment system 100 illustrated in FIG. 1. For example, the process 800 illustrated in FIG. 8 may be stored in the storage 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

In 802, a first spatial position of a second marker when a couch is at a first working position may be determined. Operation 802 may be performed by the processing module 506. In some embodiments, the second marker (e.g., the second marker 264-1, the second marker 264-2, . . . , the second marker 264-N) may include an optically detectable marker as described in the connection with FIG. 2. The first working position may correspond to a position where an imaging device (e.g., the CT device 220) in a medical device (e.g., the RT-CT 200) is located.

In some embodiments, the first spatial position of the second marker may be obtained from a prior measurement.

For example, the information regarding the first spatial position of the second marker may be retrieved from a storage (e.g., the storage 130, the storage module 508, etc.). The first spatial position of the second marker may be denoted by a second coordinate system applied to the imaging device (e.g., the CT device 220) or the treatment device (e.g., the RT device 240) as described elsewhere in the disclosure. See, for example, FIG. 2 and FIG. 6 and descriptions thereof. For example, the first spatial position of the second marker may be denoted by a first three-dimension coordinate corresponding to the second coordinate system.

In 804, a second spatial position of the second marker when the couch is at a second working position may be determined. Operation 804 may be performed by the processing module 506. In some embodiments, the second working position may correspond to a position where a treatment device (e.g., the RT device 240) in the medical device (e.g., the RT-CT 200) is located. The second spatial position of the second marker may be denoted by the second coordinate system applied to the imaging device (e.g., the CT device 220) or the treatment device (e.g., the RT device 240) as described elsewhere in the disclosure. See, for example, FIG. 2 and description thereof. For example, the second spatial position of the second marker may be denoted by a second three-dimension coordinate corresponding to the second coordinate system.

In some embodiments, the second spatial position of the second marker may be determined based on data relating to the second marker acquired by a positioning device (e.g., the positioning device 280 as illustrated in FIG. 2). In some embodiments, the data relating to the second marker may include an optical image relating to the second marker acquired by the positioning device (e.g., a camera). The second spatial position of the second marker may be determined based on the optical image and first transformation data (e.g., a first transformation equation or algorithm) between a third coordinate system applied to the positioning device and a fourth coordinate system applied to the optical image. The first transformation data (e.g., a first transformation equation or algorithm) between the third coordinate system applied to the positioning device and the fourth coordinate system applied to the optical image may be determined based on a camera calibration. The camera calibration may be obtained from a prior measurement. For example, the information regarding the camera calibration may be retrieved from a storage (e.g., the storage 130, the storage module 508, etc.). The second spatial position of the second marker determined based on the first transformation data may be denoted by the third coordinate system. For example, the second spatial position of the second marker determined based on the first transformation data may be denoted by a second three-dimension coordinate corresponding to the third coordinate system. Then, the first three-dimension coordinate corresponding to the second coordinate system may be determined based on second transformation data between the second coordinate system and the third coordinate system. The second transformation data may be obtained from a prior measurement. For example, the information regarding the second transformation data may be retrieved from a storage (e.g., the storage 130, the storage module 508, etc.).

In some embodiments, the data relating to the second marker may include movement data of the second marker detected by the positioning device (e.g., a displacement sensor, a speed sensor, an acceleration sensor, a range finder (e.g., a laser interferometer, an ultrasonic range finder, etc.), etc.). The movement data of the second marker may include, a displacement of the second marker, a speed of the second marker, an acceleration of the second marker, a movement direction of the second marker, etc. As used herein, the displacement of the second marker may refer to a location change in space when the couch moves from the first working position to the second working position. The second spatial position of the second marker may be determined based on the displacement of the second marker. In some embodiments, the displacement of the second marker may be acquired from the positioning device directly. In some embodiments, the displacement of the second marker may be determined based on other movement data (e.g., the speed of the second marker, the acceleration of the second marker, the movement direction of the second marker, etc.) by the processing module 506. For example, the acceleration of the second marker may be acquired by the positioning device (e.g., an acceleration sensor). The processing module 506 may process the acceleration of the second marker by performing a double integral on the acceleration of the second marker to determine the displacement of the second marker. As another example, the displacement of the second marker may be determined based on a laser triangulation algorithm. Furthermore, the positioning device (e.g., a laser interferometer) may emit a laser to the couch, and the couch may reflect the laser to the positioning device (e.g., a laser interferometer). The displacement of the couch may be determined based on the reflected laser and the emitting laser by using the laser triangulation algorithm.

In 806, a second spatial position of a first marker may be determined based on a first spatial position of the first marker, the first spatial position of the second marker, and the second spatial position of the second marker. Operation 806 may be performed by the processing module 506. The first spatial position of the first marker may be determined according to operation 604 as described in connection with FIG. 6. In some embodiments, a position relationship between the first marker and the second marker may be determined based on the first spatial position of the first marker and the first spatial position of the second marker. When the couch moves from the first working position to the second working position, the position relationship between the first marker and the second marker may be unchanged. The second spatial position of the first marker may be determined based on the second spatial position of the second marker and the position relationship between the first marker and the second marker.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 802 may be unnecessary. Then, a spatial position relationship between the first marker and the second marker may be obtained and/or determined based on a prior measurement. For example, the information regarding the spatial position relationship between the first marker and the second marker may be retrieved from a storage (e.g., the storage 130, the storage module 508, etc.).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system". Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially," For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for a medical device including a couch, comprising:
a computer-readable storage medium storing executable instructions, and
at least one processor in communication with the computer-readable storage medium, when executing the executable instructions, causing the system to implement a method, comprising:
obtaining a first image acquired by a first device of the medical device, the first image including a target point and a first reference point, the target point corresponding to at least one part of a subject, the first reference point corresponding to a first marker disposed on the couch of the medical device;
determining, based on the first image, a first spatial position of the first marker, the first spatial position corresponding to a first working position of the couch where the first device is located;
determining a second spatial position of the first marker corresponding to a second working position of the couch where a second device of the medical device is located;
determining, based on a difference between the first spatial position and the second spatial position, a position relationship between the at least one part of the subject and an isocenter of the second device when the couch is at the second working position; and
causing an adjustment of the second working position of the couch based on the position relationship.

2. The method of claim 1, wherein the determining a first spatial position of the first marker based on the first image, further comprises:
determining first transformation data relating to a first coordinate system applied to the first image and a second coordinate system applied to the medical device; and
determining the first spatial position of the first marker based on the first transformation data.

3. The system of claim 1, wherein the determining a second spatial position of the first marker further comprises:
determining a displacement of the first marker when the couch of the medical device moves from the first working position to the second working position based on a laser triangulation algorithm; and
determining the second spatial position of the first marker based on the displacement of the first marker.

4. The system of claim 1, wherein the determining a second spatial position of the first marker, further comprises:
determining a first spatial position of a second marker, the second marker being disposed on the couch of the medical device relative to the first marker;
determining a second spatial position of the second marker; and
determining the second spatial position of the first marker based on the first spatial position of the first marker, the first spatial position of the second marker, and the second spatial position of the second marker.

5. The system of claim 4, wherein the determining a second spatial position of the second marker further comprises:
acquiring a second image including a second reference point, the second reference point corresponding to the second marker; and
determining the second spatial position of the second marker based on the second image.

6. The system of claim 4, wherein the determining a second spatial position of the second marker, further comprises:
determining a displacement of the second marker when the couch of the medical device moves from the first working position to the second working position based on a laser triangulation algorithm; and
determining the second spatial position of the second marker based on the displacement of the second marker and the first spatial position of the second marker.

7. The system of claim 1, where the determining, based on a difference between the first spatial position and the second spatial position, a position relationship between the at least one part of the subject and an isocenter of the second device when the couch is at the second working position includes:
determining, based on the first image, a position relationship between the at least one part of the subject and an isocenter of the first device when the couch is at the first working position; and
determining, based on the position relationship between the at least one part of the subject and the isocenter of the first device and the difference between the first spatial position and the second spatial position of the first marker, the position relationship between the at least one part of the subject and the isocenter of the second device.

8. The system of claim 7, wherein the determining, based on the first image, a position relationship between the at least one part of the subject and an isocenter of the first device includes:
determining, based on the first image, a position relationship between the at least one part of the subject and the first spatial position of the first marker when the couch is at the first working position;
determining a position relationship between the isocenter of the first device and the first spatial position of the first marker; and
determining the position relationship between the at least one part of the subject and the isocenter of the first device based on the position relationship between the at least one part of the subject and the first spatial position of the first marker and the position relationship between the first spatial position of the first marker and the isocenter of the first device.

9. The system of claim 7, wherein the determining, based on the position relationship between the at least one part of the subject and the isocenter of the first device and the difference between the first spatial position and the second spatial position of the first marker, the position relationship between the at least one part of the subject and the isocenter of the second device includes:
determining, based on the difference between the first spatial position and the second spatial position of the first marker, a deformation measurement of the couch at the second working position relative to the first working position; and
determining, based on the deformation measurement of the couch and the position relationship between the at least one part of the subject and the isocenter of the first device, the position relationship between the at least one part of the subject and the isocenter of the second device.

10. The system of claim 1, wherein the determining, based on a difference between the first spatial position and the second spatial position, a position relationship between the at least one part of the subject and an isocenter of the second device of the medical device when the couch is at the second working position includes:
   determining, based on the first image, a position relationship between the first marker and the at least one part of the subject;
   determining, based on the second spatial position of the first marker, a position relationship between the isocenter of the second device and the second spatial position of the first marker; and
   determining, based on the position relationship between the isocenter of the second device and the second spatial position of the first marker and the position relationship between the first marker and the at least one part of the subject, the position relationship between the isocenter of the second device and the at least one part of the subject when the couch is at the second working position.

11. A system for a medical device including a couch, comprising:
   a computer-readable storage medium storing executable instructions, and
   at least one processor in communication with the computer-readable storage medium, when executing the executable instructions, causing the system to implement a method, comprising:
      acquiring a first image acquired by a first device of the medical device, the first image including a target point and a first reference point, the target point corresponding to at least one part of a subject, the first reference point corresponding to a first marker disposed on the couch of the medical device;
      determining, based on the first image, a first spatial position of the first marker, the first spatial position corresponding to a first working position of the couch;
      determining, based on the first image, a position relationship between the first marker and the at least one part of the subject;
      acquiring a second image including a second reference point, the second reference point corresponding to a second marker disposed on the couch;
      determining, based on the second image, a second spatial position of the second marker, the second spatial position corresponding to a second working position of the couch;
      determining, based on the second spatial position of the second marker, a second spatial position of the first marker; and
      causing an adjustment of the second working position of the couch based on the second spatial position of the first marker and the position relationship between the first marker and the at least one part of the subject.

12. The system of claim 11, wherein the first marker includes a radiologically detectable marker.

13. The system of claim 11, wherein the causing an adjustment of the second working position of the couch based on the second spatial position of the first marker and the position relationship between the first marker and the at least one part of the subject includes:
   determining, based on the second spatial position of the first marker, a position relationship between an isocenter of a second device and the second spatial position of the first marker; and
   determining, based on the position relationship between the isocenter of the second device and the second spatial position of the first marker and the position relationship between the first marker and the at least one part of the subject, a position relationship between the isocenter of the second device and the at least one part of the subject when the couch is at the second working position; and
   causing the adjustment of the second working position of the couch based on the position relationship between the isocenter of the second device and the at least one part of the subject when the couch is at the second working position.

14. The system of claim 11, wherein the first marker is disposed inside the couch.

15. The system of claim 11, wherein the second marker includes at least one portion of the couch.

16. The system of claim 11, wherein the second marker is detected by at least one of a photoelectric sensor, a laser interferometer, or a camera.

17. The system of claim 11, wherein the second marker includes an optically detectable marker.

18. The system of claim 11, wherein the second marker is disposed on a bottom of the couch.

19. A system for a medical device including a couch, comprising:
   a computer-readable storage medium storing executable instructions, and
   at least one processor in communication with the computer-readable storage medium, when executing the executable instructions, causing the system to implement a method, comprising:
      acquiring a first image including a target point and a first reference point, the target point corresponding to at least one part of a subject, the first reference point corresponding to a marker disposed on the couch of the medical device;
      determining, based on the first image, a first spatial position of the first marker, the first spatial position corresponding to a first working position of the couch;
      determining, based on the first image, a position relationship between the marker and the at least one part of the subject;
      acquiring a second image including a second reference point representing the marker when the couch is at a second working position;
      determining, based on the second image, a second spatial position of the marker; and
      causing an adjustment of the second working position of the couch based on the second spatial position of the marker and the position relationship between the marker and the at least one part of the subject.

20. The system of claim 19, wherein the marker includes a radiologically and optically detectable marker.

* * * * *